United States Patent
Wang et al.

(10) Patent No.: US 11,220,060 B2
(45) Date of Patent: Jan. 11, 2022

(54) BIOPRINTER TEMPERATURE CONTROL SYSTEM AND BIOPRINTER

(71) Applicant: REVOTEK CO., LTD, Sichuan (CN)

(72) Inventors: Deming Wang, Chengdu (CN); Xuemin Wen, Chengdu (CN); Yijun Li, Chengdu (CN); Leqing Zhang, Chengdu (CN)

(73) Assignee: Revotek Co., Ltd, Sichuan (CN)

( * ) Notice: Subject to any disclaimer, the term of this patent is extended or adjusted under 35 U.S.C. 154(b) by 481 days.

(21) Appl. No.: 16/067,563

(22) PCT Filed: Dec. 30, 2015

(86) PCT No.: PCT/CN2015/099870
§ 371 (c)(1),
(2) Date: Jun. 29, 2018

(87) PCT Pub. No.: WO2017/113190
PCT Pub. Date: Jul. 6, 2017

(65) Prior Publication Data
US 2019/0009474 A1 Jan. 10, 2019

(51) Int. Cl.
*B29C 64/393* (2017.01)
*G05D 23/30* (2006.01)
(Continued)

(52) U.S. Cl.
CPC ........ *B29C 64/393* (2017.08); *B29C 35/0288* (2013.01); *B29C 64/209* (2017.08);
(Continued)

(58) Field of Classification Search
None
See application file for complete search history.

(56) References Cited

U.S. PATENT DOCUMENTS

| 5,649,277 A | 7/1997 | Greul et al. |
| 2003/0128267 A1 | 7/2003 | Teung et al. |
| (Continued) | | |

FOREIGN PATENT DOCUMENTS

| CN | 2521042 Y | 11/2002 |
| CN | 202088668 U | 12/2011 |
| (Continued) | | |

OTHER PUBLICATIONS

International Search Report and Written Opinion for PCT/CN2015/099870, dated Oct. 13, 2016.
(Continued)

*Primary Examiner* — Joseph S Del Sole
*Assistant Examiner* — Manley L Cummins, IV
(74) *Attorney, Agent, or Firm* — Wolf, Greenfield & Sacks, P.C.

(57) ABSTRACT

The present invention relates to the technical field of a bioprinter, and in particular relates to a bioprinter temperature control system and a bioprinter. The bioprinter temperature control system provided by the present invention, comprises a flow channel temperature control system, for controlling a temperature of a flow channel between an outlet of a bioprinting material container of a bioprinter and a nozzle of the bioprinter, such that the temperature of the flow channel conforms to a desired temperature of a biological printing material. The temperature control system of the present invention can realize the temperature control of the biological printing material, improving the survival rate of the printing material, and ensuring the biological function of the printing material.

16 Claims, 4 Drawing Sheets

(51) Int. Cl.
*B33Y 50/02* (2015.01)
*B29C 35/02* (2006.01)
*C12M 1/26* (2006.01)
*B29C 64/321* (2017.01)
*B33Y 30/00* (2015.01)
*B33Y 40/00* (2020.01)
*B29C 64/255* (2017.01)
*B29C 64/295* (2017.01)
*B29C 64/209* (2017.01)
*F25B 21/04* (2006.01)

(52) U.S. Cl.
CPC .......... *B29C 64/255* (2017.08); *B29C 64/295* (2017.08); *B29C 64/321* (2017.08); *B33Y 30/00* (2014.12); *B33Y 40/00* (2014.12); *B33Y 50/02* (2014.12); *C12M 33/00* (2013.01); *G05D 23/30* (2013.01); *F25B 21/04* (2013.01)

(56) References Cited

U.S. PATENT DOCUMENTS

| | | | | |
|---|---|---|---|---|
| 2011/0176263 | A1* | 7/2011 | Yamazaki | G11C 5/063 |
| | | | | 361/679.01 |
| 2012/0089238 | A1 | 4/2012 | Kang | |
| 2015/0037445 | A1* | 2/2015 | Murphy | C12M 21/08 |
| | | | | 425/131.1 |
| 2015/0096717 | A1* | 4/2015 | Batchelder | B29C 48/802 |
| | | | | 165/64 |
| 2015/0108687 | A1* | 4/2015 | Snyder | B29C 64/118 |
| | | | | 264/308 |
| 2015/0165676 | A1* | 6/2015 | Chen | B29C 64/118 |
| | | | | 425/170 |
| 2015/0331412 | A1* | 11/2015 | Adair | G05B 19/4145 |
| | | | | 700/126 |
| 2016/0193778 | A1* | 7/2016 | Lee | B29C 64/364 |
| | | | | 425/378.1 |
| 2016/0236408 | A1* | 8/2016 | Wolf | B29C 64/209 |
| 2017/0157826 | A1* | 6/2017 | Hishiki | B29C 48/2888 |
| 2017/0172765 | A1* | 6/2017 | Solorzano | B29C 64/295 |
| 2018/0243478 | A1* | 8/2018 | Pang | B29C 64/112 |
| 2018/0281280 | A1* | 10/2018 | Solorzano | B33Y 30/00 |

FOREIGN PATENT DOCUMENTS

| | | |
|---|---|---|
| CN | 203818767 U | 9/2014 |
| CN | 104786500 A | 7/2015 |
| CN | 104802413 A | 7/2015 |
| CN | 104908324 A | 9/2015 |
| CN | 104960206 A | 10/2015 |
| CN | 105652922 A | 6/2016 |
| CN | 205364554 U | 7/2016 |
| JP | 2001-018257 A | 1/2001 |
| JP | 2004-071969 A | 3/2004 |
| JP | 11-170340 A | 9/2011 |
| WO | WO 2017/040975 A1 | 3/2017 |

OTHER PUBLICATIONS

Extended European Search Report and Search Opinion for PCT/CN2015/099870, dated Jul. 12, 2019.

Japanese Office Action dated Oct. 8, 2019 in connection with JP Patent Application No. 2018-534104.

* cited by examiner

BIOPRINTER TEMPERATURE CONTROL SYSTEM AND BIOPRINTER

RELATED APPLICATION

This Application is a national stage filing under 35 U.S.C. 371 of International Patent Application Serial No. PCT/CN2015/099870, filed Dec. 30, 2015, entitled "BIOPRINTER TEMPERATURE CONTROL SYSTEM AND BIOPRINTER". The entire contents of these applications are incorporated herein by reference in their entirety.

TECHNICAL FIELD

The present invention relates to the technical field of a bioprinter, and in particular relates to a bioprinter temperature control system and a bioprinter.

BACKGROUND ART 3D bioprinting refers to a technology of printing biological materials (including natural biological materials and synthetic biological materials or cellular solutions) into a designed three-dimensional structure based on 3D printing principles and methods. Since the printing material of the 3D bioprinting is biological material, compared with the ordinary 3D printing technology, one characteristic of the bioprinter lies in that it needs to provide the printing material with the conditions suitable for its survival, growth, and favorable biological function, while temperature is one important control index thereof.

At present, a bioprinter is generally provided with a temperature control system for controlling the temperature of a bioprinting material container, which usually includes a heat exchange member and a heat dissipation device, wherein the heat exchange member is configured to perform heat exchange with the bioprinting material container by a heat conducting jacket, and the heat dissipation device is configured to effectuate heat exchange between the heat exchange member and the environment. However, the existing bioprinter temperature control system has problems as follows:

(1) For the existing bioprinter temperature control system, the biological material is prone to clogging. One of the reasons lies in that the bioprinter temperature control system can only control the temperature of the bioprinting material container, but cannot control the temperature of the nozzle portion and the flow channel portion. At the same time, since the biological material is with a certain viscosity, the printing material is prone to clogging in the nozzle and flow channel portions where the temperature is not effectively controlled. This phenomenon, which becomes more apparent as the viscosity of the printing material increases, affects the printing efficiency of the entire bioprinter. Especially when the printing plane is non-planar, the problem is more pronounced when a long nozzle is used to better adapt to the printing requirements. In addition, the existing bioprinter temperature control system is difficult to apply to a printing material whose flow characteristics vary with the change of the temperature, resulting in the existing bioprinter is confronted with a great restriction in selecting printing material.

(2) It is difficult for the existing bioprinter temperature control system to uniformly control temperature of the bioprinting container. In the prior art, due to the reasons such as space restriction, the heat exchange member cannot comprehensively cover the heat conducting jacket, and a blind area that is not covered by the heat exchange member easily appears on the heat conducting jacket, which easily causes uniform heating on the bioprinting material container and the biological material, resulting in increased risks such as a decline in the survival rate of the biological material, and a degradation in the biological function. However, if the heat exchange member is fully covered on the heat conducting jacket, it is difficult to lay out the radiation means on the heat exchange member, and the heat exchange member usually can only be attached to an exterior of the entire structure, resulting in the overall structure projects outwards, which is unfavorable for the arrangement of the overall structure.

CONTENT OF THE INVENTION

One technical problem to be solved by the present invention is that: the existing bioprinter temperature control system does not perform temperature control on the biological material in the flow channel from the bioprinting container to the nozzle, resulting in the clogging of the biological material with poor fluidity in the flow channel. Moreover, as the temperature of the biological material in the flow channel is not controlled, risks such as a low survival rate and a degradation in the biological function of the biological material occur.

In order to solve the aforementioned technical problems, the present invention provides a bioprinter temperature control system, which comprises a flow channel temperature control system for controlling a temperature of a flow channel between an outlet of a bioprinting material container of a bioprinter and a nozzle of the bioprinter, such that the temperature of the flow channel conforms to a desired temperature of a biological printing material.

Further, the bioprinter temperature control system comprises a container temperature control system, wherein the container temperature control system comprises a container temperature control system comprising a heat exchange device, for exchanging heat with the bioprinting material container, so as to control the temperature of the bioprinting material container to conform to the desired temperature of the biological printing material in the bioprinting material container; and a first heat equalizing plate, provided between the bioprinting material container and the heat exchange device, wherein the first heat equalizing plate is configured to uniformly transfer heat between the heat exchange device and the bioprinting material container.

Further, the heat exchange device comprises a heat exchange member and a heat dissipation device, wherein the heat exchange member is configured to heat or cool the bioprinting material container, the first heat equalizing plate is disposed between the bioprinting material container and a first side of the heat exchange member, and a second side of the heat exchange member is connected with the heat dissipation device, the heat dissipation device for transferring heat between the heat exchange member and the environment.

Furthermore, the container temperature control system further comprises a second heat equalizing plate, being provided between the second side of the heat exchange member and the heat dissipation device, for uniformly exchanging heat between the heat exchange member and the heat dissipation device.

Further, the heat dissipation device comprises a heat sink assembly and a radiation fan, wherein the heat sink assembly is connected with the second side of the heat exchange member, the radiation fan is configured to transfer heat between the heat sink assembly and the environment, and the second heat equalizing plate is disposed between the second side of the heat exchange member and the heat sink assembly, for uniformly exchanging heat between the heat exchange member and the heat sink assembly.

Further, an air outlet of the radiation fan is disposed opposite to a printing platform of the bioprinter.

Further, the radiation fan is a governor fan, and the container temperature control system comprises a radiation temperature detection and control device, for detecting a temperature of the heat sink assembly, controlling whether the radiation fan is turned on and adjusting a rotation speed of the radiation fan according to a difference between the temperature of the heat sink assembly and a temperature of the environment.

Further, the container temperature control system comprises a container temperature detection and control device, for detecting a temperature of the bioprinting material container and feeding the detected temperature back to the heat exchange device to form a closed loop control of the temperature of the bioprinting material container.

Further, the bioprinter temperature control system further comprises a nozzle temperature control system for controlling a temperature of the nozzle of the bioprinter, such that a temperature of the nozzle conforms to the desired temperature of the biological printing material.

Further, the nozzle temperature control system comprises a nozzle heat conducting block provided at an outer periphery of the nozzle.

Further, the flow channel temperature control system comprises a flow channel heat conducting block, provided on an outer periphery of a flow channel between the outlet of the bioprinting material container and the nozzle.

Further, the bioprinter temperature control system comprises two independent container temperature control systems, one of which is configured to perform temperature control on a first material container of the bioprinting material container, and the other of which is configured to perform temperature control on a second material container of the bioprinting material container.

Further, the heat exchange member comprises a semiconductor refrigeration slice.

The present invention further provides a bioprinter, which comprises the aforementioned bioprinter temperature control system.

Further, the bioprinter comprises a bioprinting material container including a first material container and a second material container, wherein a nozzle of the bioprinter communicates with an outlet of one of the first material container and the second material container through the flow channel, and a flow channel heat conducting block is provided on an outer periphery of the flow channel.

Further, a nozzle heat conducting block is provided on an outer periphery of the nozzle, and the flow channel sequentially passes through the flow channel heat conducting block and the nozzle heat conducting block from the outlet to communicate with the nozzle.

Further, a heat insulating layer is provided on an outer periphery of the flow channel in the nozzle heat conducting block, for isolating heat from the nozzle heat conducting block.

Further, the heat insulating layer is disposed between the flow channel and the nozzle heat conducting block.

The bioprinter temperature control system in the present invention, by being provided with a flow channel temperature control system, can realize the temperature control of a flow path between the bioprinting material container and the nozzle, so that it is possible to effectively solve the current problem that the printing material is prone to clogging at the flow channel, and effectively improve the printing efficiency of the bioprinter.

Also, by providing a heat equalizing plate between the bioprinting material container and the heat exchange device, a uniform temperature control of the bioprinting material container can be achieved, thereby improving the survival rate of the printing material and ensuring the biological function of the printing material. Moreover, since the uniform temperature control of the entire bioprinting material container can be achieved without covering the heat exchange member entirely on the bioprinting material container, it is possible to facilitate a layout of the heat dissipation device, which makes the whole structure more compact and aesthetic.

In addition, by providing a nozzle temperature control system, the present invention can realize a temperature control of the nozzle, so that it is possible to effectively solve the current problem that the printing material is prone to clogging at the nozzle. Especially when the printing plane is non-planar and a longer nozzle is configured to better adapt to the printing requirement, the effect is more pronounced, and the printing efficiency of the bioprinter is effectively improved.

The present invention provides a temperature control system for a bioprinter, for controlling the temperature of the bioprinter. The temperature control makes the temperature of the bioprinter more uniform, which is favorable to improve the survival rate and the biological function of the cells, and realize a more desirable printing object.

Exemplary embodiments of the present invention are described in detail with reference to the following drawings, and then other features as well as advantages of the present invention will become explicit.

BRIEF DESCRIPTION OF THE DRAWINGS

In order to more clearly illustrate the embodiments of the present invention or the technical solutions in the prior art, a brief introduction will be given below for the drawings required to be used in the description of the embodiments or the prior art. It is obvious that, the drawings illustrated as follows are merely some of the embodiments of the present invention. For a person skilled in the art, he or she may also acquire other drawings according to such drawings on the premise that no inventive effort is involved.

Figure 1:
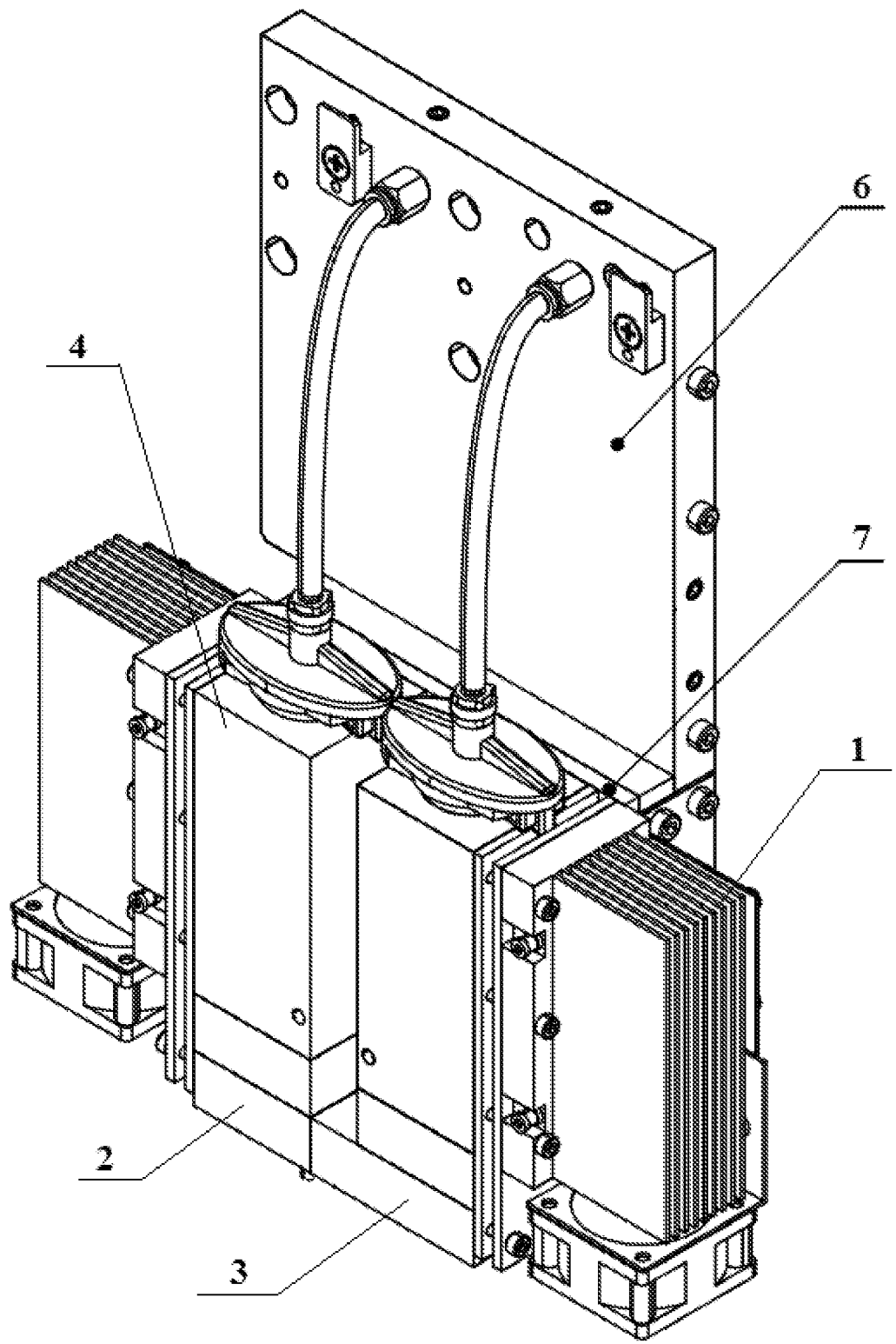
FIG. 1 shows a schematic view of the structure of the bioprinter temperature control system installed on the bioprinter according to one embodiment of the present invention.

In the drawings:
1. container temperature control system; 11. heat conducting jacket; 12. semiconductor refrigeration device; 13. heat dissipation device; 131. heat sink assembly; 132. radiation fan; 14. first heat equalizing plate; 15. second heat equalizing plate; 16. first connecting bracket; 17. second connecting bracket; 18. first temperature sensor; 19. second temperature sensor;
2. nozzle temperature control system; 21. nozzle heat conducting block;
3. flow channel temperature control system; 31. flow channel heat conducting block;

4. bioprinting material container; 41. first material container; 42. second material container;

5. nozzle; 6. mounting plate; 7. heat insulating plate.

EMBODIMENTS

Thereinafter, the technical solution in the embodiments of the present invention will be explicitly and completely described in combination in combination with the drawings in the embodiments of the present invention. Apparently, the described embodiments are merely part of the embodiments of the present invention, rather than all the embodiments. The following descriptions of at least one exemplary embodiment which are in fact merely descriptive, by no means serve as any delimitation on the present invention as well as its application or use. On the basis of the embodiments of the present invention, all the other embodiments acquired by a person skilled in the art on the premise that no inventive effort is involved fall into the protection scope of the present invention.

In the description of the present invention, it is necessary to understand that, the azimuth or positional relations indicated by such azimuth terms as "front, rear, up, down, left, right", "transverse, vertical, perpendicular, horizontal" and "top, bottom", which are usually based on the azimuth or positional relations illustrated by the drawings, are only for facilitating description of the present invention and simplifying the description. Unless otherwise specified, such azimuth terms do not indicate or imply that the device or element referred to has to present a particular azimuth or to be constructed and operated in a particular azimuth, so that it cannot be understood as limiting the protection scope of the present invention. The azimuth terms "within" and "outside" mean the interior and exterior relative to the contour of various members themselves.

In the description of the present invention, it is necessary to understand that, words such as "first" and "second" which are used to define the parts, are only intended to facilitate distinguishing the corresponding parts. Unless otherwise specified, the aforementioned words do not have particular meanings, and thus cannot be understood as limitation on the protection scope of the present invention.

In order to solve the technical problem that the printing material is prone to clogging in the nozzle and the flow channel in the prior art, FIGS. 1-4 show a schematic view of the structure of the bioprinter temperature control system according to one embodiment of the present invention. The bioprinter temperature control system of the present invention comprises a flow channel temperature control system 3 for controlling a temperature of a flow channel between an outlet of a bioprinting material container 4 and a nozzle 5, such that the temperature of the flow channel conforms to a desired temperature of a printing material. The flow channel here should not be understood to include any flow channel inside the nozzle 5. In this way, the bioprinter temperature control system of the present invention can ensure that the temperature of the flow channel also meets the requirements of the printing material, thereby ensuring a smooth flow of the printing material and improving the printing efficiency of the bioprinter.

The bioprinter temperature control system of the present invention comprises a container temperature control system 1, the container temperature control system 1 including a heat exchange device for exchanging heat with the bioprinting material container 4, so as to control the temperature of the bioprinting material container 4 to conform to the desired temperature of the printing material contained in the bioprinting material container 4; and the container temperature control system 1 further comprises a first heat equalizing plate 14 provided between the bioprinting material container 4 and the heat exchange device, wherein the first heat equalizing plate 14 is configured to uniformly transfer heat between the heat exchange device and the bioprinting material container 4.

The bioprinter temperature control system of the present invention, by being provided with the first heat equalizing plate 14 between the bioprinting material container 4 and the heat exchange device, can realize a uniform temperature control of the bioprinting material container 4, thereby improving the survival rate of the printing material, ensuring the biological function of the printing material, and preventing the of the printing material from clogging in the bioprinting material container 4, which improves the operational reliability of the bioprinter.

As an embodiment of the heat exchange device, the heat exchange device may include a heat exchange member and a heat dissipation device 13, wherein the heat exchange member is configured to heat or cool the bioprinting material container 4, and the heat dissipation device 13 is configured to exchange heat between the heat exchange member and the environment. In this way, when the temperature of the bioprinting material container 4 is higher than the desired temperature of the printing material, the heat exchange member is able to absorb heat from the bioprinting material container 4, thereby cooling the bioprinting material container 4 to the desired temperature of the printing material; and when the temperature of the bioprinting material container 4 is lower than the temperature required by the printing material, the heat exchange member is able to transfer heat to the bioprinting material container 4, thereby heating the bioprinting material container 4 to the desired temperature of the printing material. As can be seen, being configured to heat or cool the bioprinting material container 4 according to the actual conditions, the heat exchange device of the embodiment can control the temperature of the bioprinting material container 4 in more flexible manner as well as with a higher control accuracy, and can meet the temperature requirements of different printing materials.

In order to transfer heat more uniformly between the heat exchange member and the heat dissipation device 13, a second heat equalizing plate 15 may also be disposed between the second side of the heat exchange member and the heat dissipation device 13. Based on the second heat equalizing plate 15, the heat in the environment can be transferred to the second side of the heat exchange member more uniformly via the heat dissipation device 13, thus reducing a temperature difference between both sides of the heat exchange member, and further improving the heat transfer effect of the heat exchange member.

Such structure is also favorable for the arrangement of the overall structure. Under normal circumstances, if the heat dissipation device 13 is entirely covered on the heat exchange member, the radiation fan 132 of the heat dissipation device 13 will be attached to the outside of the entire structure, which results in the entire structure projecting outwards. By providing the second heat equalizing plate 15 between the heat dissipation device 13 and the heat exchange member, the present embodiment can reduce a blind area of heat exchange on the heat exchange member, and provide an assembling space for the radiation fan 132, so as to avoid the outward projection of the entire structure.

In addition, in order to further solve the technical problem that the printing material is prone to clogging at the nozzle in the prior art, the bioprinter temperature control system of the present invention may further comprise a nozzle temperature control system 2, wherein the nozzle temperature control system 2 is used for controlling a temperature of the nozzle 5 of the bioprinter to conform to the desired temperature of the printing material.

In this way, the bioprinter temperature control system of the present invention not only ensures that the temperature of the flow channel meets the requirements of the printing material, but also ensures that the temperature of the nozzle 5 and the bioprinting material container 4 meets the requirements of the printing material, thereby ensuring a smooth flow of the printing material and improving the printing efficiency of the bioprinter. Moreover, since the printing material can be in a proper temperature environment in the whole printing process, it can also ensure that the printing material is always with a favorable biological property, thereby improving the property of a bioprinting product.

The bioprinter temperature control system of the present invention will be further described below in combination with the embodiments illustrated in FIGS. 1-4. In the embodiment, the bioprinter temperature control system is applied to a bioprinter, whose bioprinting material container 4 comprises a first material container 41 and a second material container 42, wherein the first material container 41 and the second material container 42 are connected to a mounting plate 6 of the bioprinter through a heat insulating plate 7, and the nozzle 5 of the bioprinter is disposed at the outlet of the first material container 4, while the outlet of the second material container 42 is connected to the nozzle 5 through an auxiliary material flow channel 421. The first material container 41 may serve as a main material container for containing a main material (also referred to as bio-ink), and the second material container 42 may serve as an auxiliary material container for containing an auxiliary material (such as hydrogel). For example, the auxiliary material may wrap the main material to prevent the main material from being damaged by destruction of a mechanical force subjected in the printing process. Certainly, the main material and the auxiliary material may also be combined together in other manners, such as mixing.

As shown in FIG. 1-4, in the embodiment, the bioprinter temperature control system comprises two independent container temperature control systems 1, a set of nozzle temperature control system 2, and a set of flow channel temperature control system 3, wherein one container temperature control system 1 is configured to control the temperature of the first material container 41, the other container temperature control system 1 is configured to control the temperature of the second material container 42, the nozzle temperature control system 2 is configured to control the temperature of the nozzle 5, and the flow channel temperature control system 3 is configured to control the temperature of the auxiliary material flow channel 421. By providing two independent container temperature control systems 1 to control the temperatures of the first material container 41 and the second material container 42 respectively, it is possible to satisfy different requirements for the temperature of the main material and the auxiliary material which are with different properties.

In the embodiment, the two sets container temperature control systems 1 are substantially the same in the structure, therefore, only the container temperature control system 1 disposed at the second material container 42 is taken as an example to illustrate the container temperature control system 1 in the following.

Figure 2:
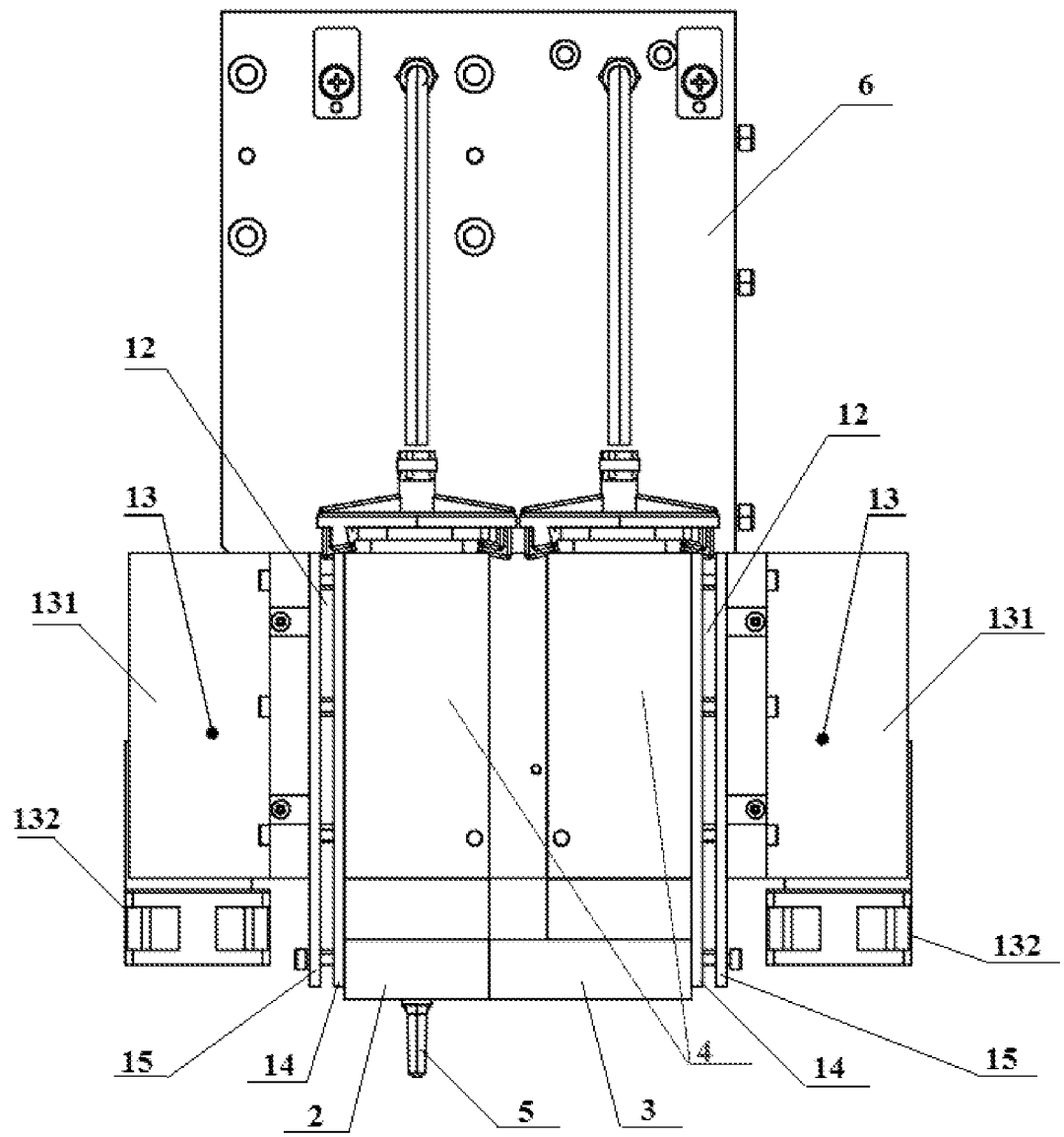
FIG. 2 shows a front view of the embodiment shown in FIG. 1.
Figure 4:
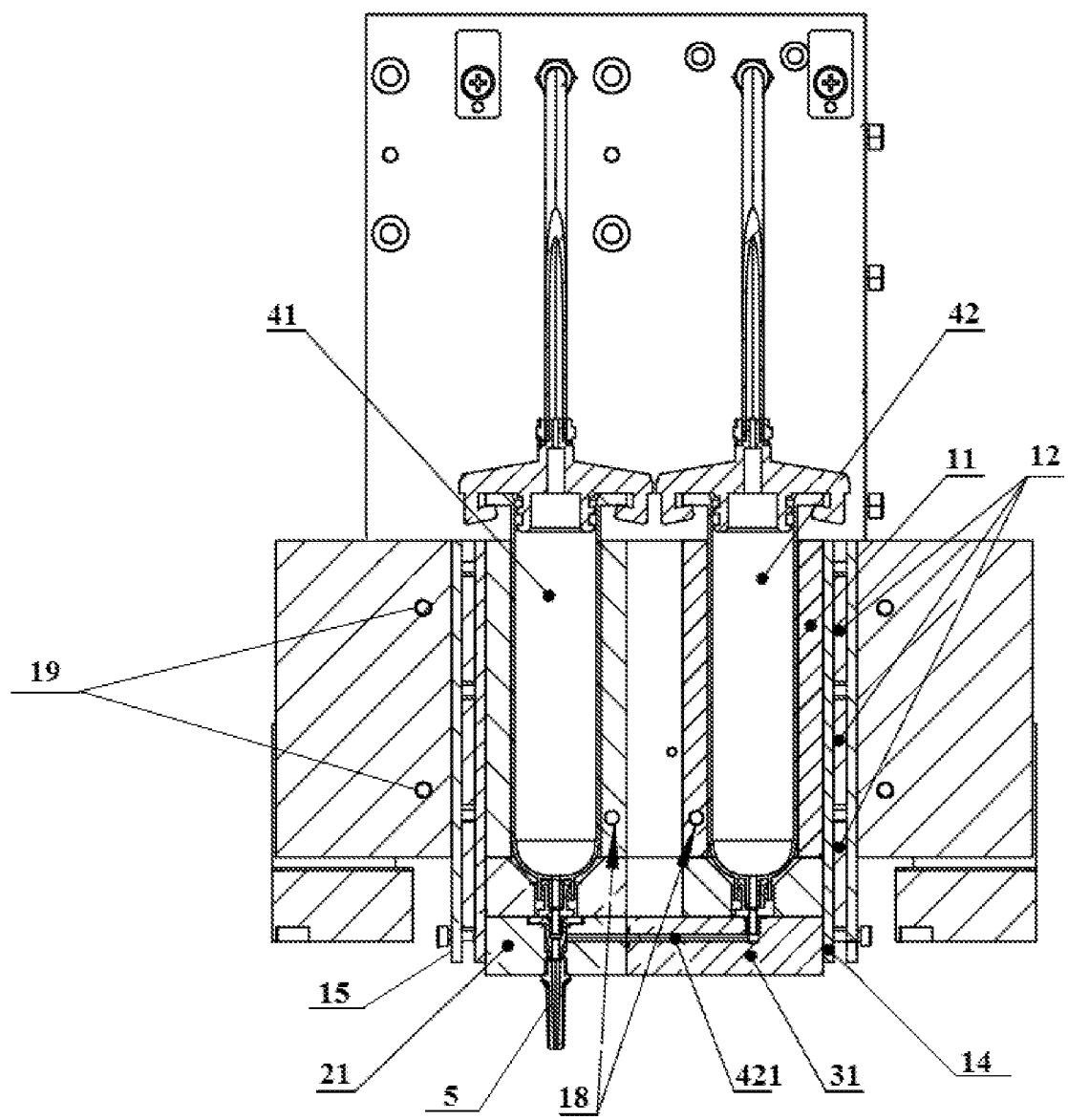
FIG. 4 shows an A-A sectional view of FIG. 3.

As shown in FIG. 2 and FIG. 4, in the embodiment, the container temperature control system 1 comprises a heat conducting jacket 11, a semiconductor refrigeration system serving as a heat exchange device, a first heat equalizing plate 14, and a second heat equalizing plate 15, wherein the semiconductor refrigeration system comprises a semiconductor refrigeration device 12 and a heat dissipation device 13, the heat conducting jacket 11 is sleeved on an outer periphery of the second material container 42, the first side of the semiconductor refrigeration device 12 is connected to the heat conducting jacket 11 through the first heat equalizing plate 14, and the second side of the semiconductor refrigeration device 12 is connected to the heat dissipation device 13 through the second heat equalizing plate 15.

The semiconductor refrigeration system can be used as both a heat source and a cold source. Base on the semiconductor refrigeration theory, when a DC voltage is applied on both sides of the semiconductor refrigeration slice of the semiconductor refrigeration system, a DC current is generated, which makes one side of the semiconductor refrigeration slice heat and the other side of the semiconductor refrigeration slice refrigerate. Typically, the heating side is called "a hot surface", while the refrigerating side is called "a cod surface". The semiconductor refrigeration slice is provided with a control end. After an instruction is sent to the control end, the voltage polarity on both sides of the semiconductor refrigeration slice can be exchanged, so that the current flows reversely, thereby realizing the mutual conversion between the cold surface and the hot surface of the semiconductor cooling fin. Also in other words, the mutual conversion between the cooling function and the heating function of the semiconductor refrigeration system can be realized. Except the conversion between the cold surface and the hot surface, it is also possible to realize an accurate temperature control (accuracy of 0.01 degrees) according to the requirements. As can be seen, by applying the semiconductor refrigeration system as the heat exchange device of the present invention, the heating or cooling of the second material container 42 can be conveniently and effectively realized to meet different temperature requirements of various biological printing materials.

In the embodiment, the container temperature control system 1 is provided with a container temperature detection and control device, which is configured to control the semiconductor refrigeration system to shift between a heating operation state and a cooling operation state. As shown in FIG. 4, in the embodiment, the container temperature detection and control device comprises a control system (not shown in the figures) and a first temperature sensor 18 provided on the heat conducting jacket 11. The first temperature sensor 18 is used for detecting a temperature of the heat conducting jacket 11 and transferring it to the control system. As the temperature of the heat conducting jacket 11 conforms to the temperature of the corresponding second material container 42, the first temperature sensor 18 is able to detect a temperature of the second material container 42 and transfer it to the control system. The control system controls an operational state of the semiconductor refrigeration system by comparing a difference between the temperature of the second material container 42 and the desired temperature of the auxiliary material (normally preset in the control system), so as to realize a closed-loop control of the temperature of the second material container 42, improving the temperature control accuracy. When the temperature of the first material container 41 and the second material container 42 detected by the first temperature sensor 18 reaches the desired temperature of the biological material, corresponding materials can be added into the first material container 41 and the second material container 42 respectively.

The first heat equalizing plate 14 disposed on the first side of the semiconductor refrigeration device 12 can transfer heat uniformly with the gas phase and the liquid phase inside being mutually converted, so that the heat transfer between the semiconductor refrigeration device 12 and the second material container 42 is more uniform and effective, so as to prevent the phenomenon of uneven heat transfer caused by the semiconductor refrigeration device 12 unable to comprehensively cover the heat conducting jacket 11. Moreover, since there is no need to cover the semiconductor refrigeration slice on the entire heat conducting jacket 11, the structural design and the spatial layout are also more simple and compact. The second heat equalizing plate 15 disposed on the second side of the semiconductor refrigeration device 12 can make the heat transfer between the semiconductor refrigeration device 12 and the environment more uniform, and reduce a temperature difference between the first side and the second side of the semiconductor refrigeration device 12. Since there is a reverse heat transfer process between the cold face and the hot face of the semiconductor refrigeration device 12, and the greater the temperature difference between the hot and cold faces is, the more apparent such reverse heat transfer effect becomes, while once the heat transferred by the forward heat transfer is equal to the heat transferred by the reverse heat transfer, the temperature of the cold and hot faces will no longer change, which affects the cooling or heating action of the semiconductor refrigeration device 12, by providing the second heat equalizing plate 15 to reduce the temperature difference between the first side and the second side of the semiconductor refrigeration device 12, it is possible to weaken the reverse heat transfer effect, and bring the cooling or heating function of the semiconductor refrigeration device 12 in adequate play.

The existing semiconductor refrigeration device 12 generally comprises only one semiconductor cooling fin. In order to improve the heat transfer power of the semiconductor refrigeration device 12, the semiconductor refrigeration device 12 of the present invention may comprise at least two semiconductor cooling fins. As shown in FIG. 4, in the embodiment, the semiconductor refrigeration device 12 comprise s three semiconductor cooling fins, which brings advantages as follows: on one hand, as the number of the semiconductor cooling fins is increased, the heating or cooling power can be effectively increased, thereby improving the heat transfer effect; on the other hand, the three semiconductor cooling fins can be parallel disposed, in this way, the operational reliability of the semiconductor refrigeration device 12 can be improved then, and even if one of the semiconductor cooling fins fails, the remaining ones can still work normally, thus ensuring a normal progress of heating or cooling. In addition, as can be known from FIG. 4, a certain clearance is provided between the three semiconductor cooling fins of the embodiment, so as to facilitate the connection and installation of the lines.

Figure 3:
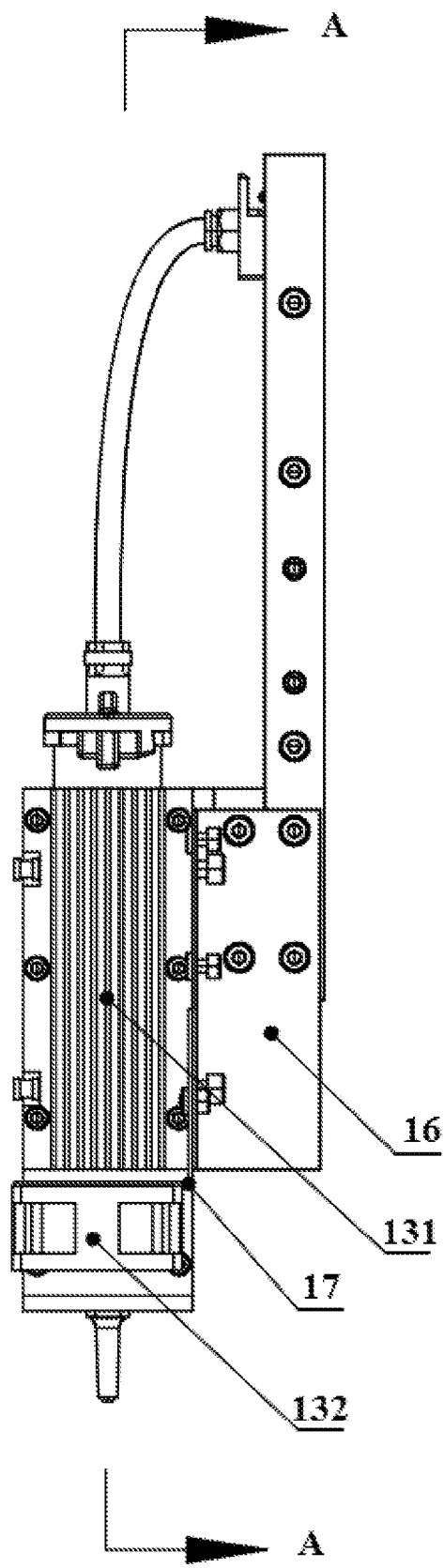
FIG. 3 shows a side view of FIG. 2.

The heat dissipation device 13 may be a water-cooled heat dissipation device or an air-cooled heat dissipation device. As shown in FIG. 2-4, in the embodiment, the heat dissipation device 13 is an air-cooled heat dissipation device, and it comprises a heat sink assembly 131 and a radiation fan 132, wherein the heat sink assembly 131 is connected to the mounting plate 6 through a first connecting bracket 16, and connected to the second side of the semiconductor refrigeration device 12 through the second heat equalizing plate 15, while the radiation fan 132 is disposed at a lower portion of the heat sink assembly 131 through a second connecting bracket 17. In this way, a uniform heat transfer can be performed between the heat sink assembly 131 and the second side of the semiconductor refrigeration device 12 through the second heat equalizing plate 15. Further, the radiation fan 132 can realize the heat transfer between the heat sink assembly 131 and the environment, such that the heat dissipation device 13 can realize heat transfer between the semiconductor refrigeration device 12 and the environment. In addition, holes (not shown in the figures) transversely penetrating the radiation fins may be provided on the radiation fins of the heat sink assembly 131, so as to increase the radiation area and improve the radiation efficiency.

In the embodiment, the air outlet of the radiation fan 132 is disposed opposite to the printing platform of the bioprinter, which is disposed upward in FIG. 1-4. This can avoid the radiation fan 132 from guiding the heat of the heat sink assembly 131 to the printing platform, so that it is possible to prevent the heat from influencing the characteristics of the biological material on the printing platform.

Further, in order to save the energy and realize accurate temperature control, the radiation fan 132 of the present invention may adopt a governor fan, and controls whether the radiation fan 132 is turned on and adjusts a rotation speed of the radiation fan 132 according to a difference between the temperature of the heat sink assembly 131 and the ambient temperature, so as to make an operational state of the radiation fan 132 conform to actual requirements, avoiding waste of the energy. In order to achieve the object, the container temperature control system 1 of the present invention may further include a radiation temperature detection and control device for detecting the temperature of the heat sink assembly 131, and controlling whether the radiation fan 132 is turned on and adjusting the rotation speed of the radiation fan 132 according to the difference between the temperature of the heat sink assembly 131 and an ambient temperature. In the embodiment shown in FIG. 4, the radiation temperature detection and control device comprises a second temperature sensor 19 and a control system which are both disposed on the heat sink assembly 131. The second temperature sensor 19 is able to detect the temperature of the heat sink assembly 131 and feedback the detected temperature to the control system. The control system compares the temperature of the heat sink assembly 131 with the ambient temperature, and controls whether the radiation fan 132 works as well as the rotational speed during operation according to the difference between the two temperatures. For example, in the case that the container temperature control system 1 works and the temperature difference $\Delta T$ between the temperature of the heat sink assembly 131 and the ambient temperature is greater than a preset value T0, the radiation fan 132 is turned on and runs at a rotation speed of $R=(\Delta T/30) \times R0$, wherein R0 is a rated rotation speed of the fan; while in the case that the container temperature control system 1 does not work or the temperature difference $\Delta T$ between the temperature of the heat sink assembly 131 and the ambient temperature is less than the preset value T0, the radiation fan 132 is controlled not to start. The control system here may be the same control same as that of the container temperature detection and control device. For example, the corresponding function may be realized by the existing control system of the bioprinter.

The operational process of the container temperature control system 1 of the embodiment is as follows:

(1) When the temperature of the second material container 42 is lower than the desired temperature of the auxiliary material, the semiconductor refrigeration system is in a heating state, in which the first side of the semiconductor refrigeration device 12 close to the second material container 42 is a hot surface, and the second side of the semiconductor refrigeration device 12 close to the heat sink assembly 131 is a cold surface. At this time, the first side of the semiconductor refrigeration device 12 transfers heat to the second material container 42 through the first heat equalizing plate 14 and the heat conducting jacket 11, so as to achieve the purpose of heating the second material container 42, rising the temperature of the second material container 42 to the desired temperature of the auxiliary material. At the same time, the heat in the environment can be transferred to the second side of the semiconductor refrigeration device 12 by the heat sink assembly 131 and the second heat equalizing plate 15, making the temperature of the second side of the semiconductor refrigeration device 12 higher, so that the temperature difference between the first side and the second side of the semiconductor refrigeration device 12 is reduced, and in other words, the temperature difference between the cold and hot surfaces of the semiconductor refrigeration device 12 is reduced, and the heating upper limit of the semiconductor refrigeration device 12 is increased.

(2) On the contrary, when the temperature of the second material container 42 is higher than the desired temperature of the auxiliary material, the semiconductor refrigeration system is in a cooling state, in which the first side of the semiconductor refrigeration device 12 close to the second material container 42 becomes a cold surface, while the second side of the semiconductor refrigeration device 12 close to the heat dissipation device 13 is becomes a hot surface. At this time, the heat of the second material container 42 is transferred to the first side of the semiconductor refrigeration device 12 through the first heat conducting jacket 11 and the first heat equalizing plate 14, i.e., the first side of the semiconductor refrigeration device 12 absorbs heat from the second material container 42, so as to achieve the purpose of lowering the temperature of the second material container 42, so that the temperature of the second material container 42 is cooled to the desired temperature of the auxiliary material. At the same time, the second side of the semiconductor refrigeration device 12 transfers heat to the heat sink assembly 131 through the second heat equalizing plate 15, and finally releases the heat to the environment under the effect of the radiation fan 132, thus reducing the temperature difference of the cold and hot surfaces of the semiconductor refrigeration device 12, and improving the cooling effect of the semiconductor refrigeration device 12.

The container temperature control system 1 of the embodiment is with characteristics such as a small volume, a quick response and a favorable controlling property. Since a set of container temperature control system 1 is provided at the first material container 41 and the second material container 42 respectively, the bioprinter temperature control system of the embodiment can respectively control the temperature of the main material and the temperature of the auxiliary material, so as to satisfy different temperature requirements of the main material and the auxiliary material, and to make the main material and auxiliary material maintain a more excellent biological performance. In addition, because of the application of a combined structure of the semiconductor refrigeration system and the heat equalizing plate, the heat transfer efficiency becomes higher, the heat transfer process becomes more uniform, and the control accuracy becomes higher, wherein the control accuracy may reach 0.01 degrees. Moreover, the heating and cooling can be bilaterally selected, so that the requirements of a plurality of biological materials as well as different operational environments can be satisfied, enabling the same bioprinter to have a wider selection range of a printing material.

As shown in FIG. 1-4, in the embodiment, the nozzle temperature control system 2 includes a nozzle heat conducting block 21, and the flow channel temperature control system 3 includes a flow channel heat conducting block 31, wherein the nozzle heat conducting block 21 is disposed below the first material container 41 and is located on an outer periphery of the nozzle 5, while the flow channel heat conducting block 31 is disposed below the second material container 42 and is located on an outer periphery of the auxiliary material flow channel 421. A first side of the nozzle heat conducting block 21 is connected to the first heat equalizing plate 14 of the container temperature control system 1 located at the first material container 41, a second side of the nozzle heat conducting block 21 is connected to a first side of the flow channel heat conducting block 31, and the second side of the flow channel heat conducting block 31 is connected to the first heat equalizing plate 14 of the container temperature control system 1 located at the second material container 42. In this way, the semiconductor refrigeration device 12 at one side of the first material container 41 can exchange heat with the nozzle 5 via the first heat equalizing plate 14 and the nozzle heat conducting block 21, realizing the temperature control of the nozzle 5; while the semiconductor refrigeration device 12 at one side of the second material container 42 can exchange heat with the auxiliary flow channel 421 through the first heat equalizing plate 14 and the flow channel heat conducting block 31, realizing the temperature control of the auxiliary material flow passage 421. It can be seen that, the embodiment can enable the temperature of the nozzle 5 and the auxiliary material flow channel 421 conform to the requirements of the printing material, which avoids the printing material (especially the high-viscosity printing material) clogging at the nozzle 5 as well as the auxiliary material flow channel 421, and is also favorable for maintaining the biological activity of the printing material.

As shown in FIG. 4, in the embodiment, the auxiliary material flow channel 421 is directly disposed in the flow channel heat conducting block 31, and the auxiliary material from the outlet of the second material container 42 flows into the nozzle 5 via the auxiliary material flow channel. By directly disposing the auxiliary material flow channel 421 in the flow channel heat conducting block 31, the flow path of the auxiliary material can be adjusted according to the demand, so as to guide the auxiliary material to a desired position.

As shown in FIG. 4, in the embodiment, a part of the auxiliary material flow channel 421 needs to pass through the nozzle heat conducting block 21 before flowing into the nozzle 5. In order to realize independent accurate temperature control of the main material and the auxiliary material, a heat insulating layer (not shown in the figures) is provided around the auxiliary material flow channel 421 in the nozzle heat conducting block 21. The heat insulating layer can ensure that the temperature inside the auxiliary material flow channel 421 is free from the influence of the temperature of the nozzle heat conducting block 21 through.

The bioprinter temperature control system of the present invention is not limited to be configured in the manner of the embodiment, but can be adaptively configured according to the specific structural relations of the bioprinting material container 4, the nozzle 5 and the flow channel of the bioprinter. For example, if the bioprinter only includes one bioprinting material container 4, the bioprinter temperature control system may include only one container temperature control system 1. If the bioprinter is further provided with a long main material flow channel between the outlet of the first material container 41 and the nozzle 5, the flow channel temperature control system 3 may also be used to control the temperature of the main material flow channel, and the like. These configuration manners are all within the protection scope of the present invention.

The bioprinter provided by the present invention comprises a bioprinting material container 4 and the bioprinter temperature control system of the present invention. The heat conducting jacket 11 of the container temperature control system 1 of the bioprinter temperature control system is disposed on an outer periphery of the bioprinting material container 4.

The foregoing is intended only as an exemplary of the present invention, but is not used for limiting the present invention. Any amendment, equivalent replacement, improvement, and the like within the spirit and principles of the present invention should all be contained within the protection scope of the present invention.

The invention claimed is:

1. A bioprinter temperature control system, comprising:
a flow channel temperature control system, for controlling a temperature of a flow channel between an outlet of a bioprinting material container of a bioprinter and a nozzle of the bioprinter, such that the temperature of the flow channel conforms to a desired temperature of a biological printing material; and
a container temperature control system comprising:
a heat exchange device, for exchanging heat with the bioprinting material container, so as to control the temperature of the bioprinting material container to conform to the desired temperature of the biological printing material in the bioprinting material container; and
a first heat equalizing plate, provided between the bioprinting material container and the heat exchange device, wherein the first heat equalizing plate is configured to uniformly transfer heat between the heat exchange device and the bioprinting material container;
wherein the heat exchange device comprises a heat exchange member and a heat dissipation device, wherein the heat exchange member is configured to heat or cool the bioprinting material container, the first heat equalizing plate is disposed between the bioprinting material container and a first side of the heat exchange member, and a second side of the heat exchange member is connected with the heat dissipation device, the heat dissipation device for transferring heat between the heat exchange member and the environment.

2. The bioprinter temperature control system according to claim 1, wherein the container temperature control system further comprises a second heat equalizing plate, being provided between the second side of the heat exchange member and the heat dissipation device, for uniformly exchanging heat between the heat exchange member and the heat dissipation device.

3. The bioprinter temperature control system according to claim 2, wherein the heat dissipation device comprises a heat sink assembly and a radiation fan, wherein the heat sink assembly is connected with the second side of the heat exchange member, the radiation fan is configured to transfer heat between the heat sink assembly and the environment, and the second heat equalizing plate is disposed between the second side of the heat exchange member and the heat sink assembly, for uniformly exchanging heat between the heat exchange member and the heat sink assembly.

4. The bioprinter temperature control system according to claim 3, wherein an air outlet of the radiation fan is disposed opposite to a printing platform of the bioprinter.

5. The bioprinter temperature control system according to claim 3, wherein the radiation fan is a governor fan, and the container temperature control system comprises a radiation temperature detection and control device, for detecting a temperature of the heat sink assembly, controlling whether the radiation fan is turned on and adjusting a rotation speed of the radiation fan according to a difference between the temperature of the heat sink assembly and a temperature of the environment.

6. The bioprinter temperature control system according to claim 1, wherein the container temperature control system comprises a container temperature detection and control device, for detecting a temperature of the bioprinting material container and feeding the detected temperature back to the heat exchange device to form a closed loop control of the temperature of the bioprinting material container.

7. The bioprinter temperature control system according to claim 1, further comprising a nozzle temperature control system for controlling a temperature of the nozzle of the bioprinter, such that a temperature of the nozzle conforms to the desired temperature of the biological printing material.

8. The bioprinter temperature control system according to claim 7, wherein the nozzle temperature control system comprises a nozzle heat conducting block provided on an outer periphery of the nozzle.

9. The bioprinter temperature control system according to claim 1, wherein the flow channel temperature control system comprises a flow channel heat conducting block, provided on an outer periphery of a flow channel between the outlet of the bioprinting material container and the nozzle.

10. The bioprinter temperature control system according to claim 1, wherein the container temperature control system is a first container temperature control system and the bioprinter temperature control system further comprises a second container temperature control system independent of the first temperature control system, wherein the first temperature control system is configured to perform temperature control on a first material container of the bioprinting material container, and the second container temperature control system is configured to perform temperature control on a second material container of the bioprinting material container.

11. The bioprinter temperature control system according to claim 1, wherein the heat exchange member comprises a semiconductor refrigeration slice.

12. A bioprinter, comprising the bioprinter temperature control system according to claim 1.

13. The bioprinter according to claim 12, comprising a bioprinting material container, the bioprinting material container comprising a first material container and a second material container, wherein a nozzle of the bioprinter communicates with an outlet of one of the first material container and the second material container through the flow channel, and a flow channel heat conducting block is provided on an outer periphery of the flow channel.

14. The bioprinter according to claim 13, wherein a nozzle heat conducting block is provided on an outer periphery of the nozzle, and the flow channel sequentially passes through the flow channel heat conducting block and the nozzle heat conducting block from the outlet to communicate with the nozzle.

15. The bioprinter according to claim 14, wherein a heat insulating layer is provided on an outer periphery of the flow channel in the nozzle heat conducting block, for isolating heat from the nozzle heat conducting block.

16. The bioprinter according to claim 15, wherein the heat insulating layer is disposed between the flow channel and the nozzle heat conducting block.

* * * * *